United States Patent [19]

Lee et al.

[11] Patent Number: 5,110,903
[45] Date of Patent: May 5, 1992

[54] PROCESS FOR THE PREPARATION OF MIXED PARYLENE DIMERS FREE OF ALPHA-HALOGENS

[75] Inventors: Chinsoo Lee; David R. Bassett, both of Charleston, W. Va.

[73] Assignee: Union Carbide Chemicals & Plastics Technology Corporation, Danbury, Conn.

[21] Appl. No.: 630,548

[22] Filed: Dec. 20, 1990

[51] Int. Cl.$^5$ .............................................. C07C 17/00
[52] U.S. Cl. .................................. 528/397; 564/289; 570/190; 585/469
[58] Field of Search ....................... 528/397; 564/289; 570/190; 585/469

[56] References Cited

U.S. PATENT DOCUMENTS

| | | | |
|---|---|---|---|
| 3,947,371 | 3/1976 | Parent et al. | 428/405 |
| 4,163,828 | 8/1979 | Mahoney | 428/411 |
| 4,500,562 | 3/1983 | Jahn et al. | 427/27 |
| 4,675,462 | 6/1987 | Ungarelli et al. | 585/428 |
| 4,769,505 | 9/1988 | Lee et al. | 585/428 |
| 4,806,702 | 2/1989 | Lee et al. | 585/429 |
| 4,849,559 | 7/1989 | Lee et al. | 570/190 |

FOREIGN PATENT DOCUMENTS 0183083 10/1985 European Pat. Off. .
0253191 6/1987 European Pat. Off. .

Primary Examiner—John Kight, III.
Assistant Examiner—Shelley A. Wright
Attorney, Agent, or Firm—Warren K. Volles

[57] ABSTRACT

A process is provided for the preparation of a mixture of parylene dimers wherein the distribution of dimers within the mixture is predetermined by the proper selection of halogenated and non-halogenated 2,2-paracyclophane starting material. Since the dimers are free of alpha-halogens, the formation of environmentally undesirable acid halides during the deposition of parylene films and coatings is avoided. Since the dimers are useful in the preparation of inert, transparent, conformal coatings of parylene, desirable chemical and/or physical properties can be imparted to such coating by formation of a dimer mixture of a predetermined composition. The parylene film properties, composition and deposition conditions will be different by varying dimer distribution.

21 Claims, 1 Drawing Sheet

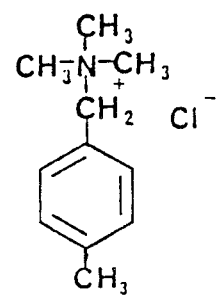
(I)
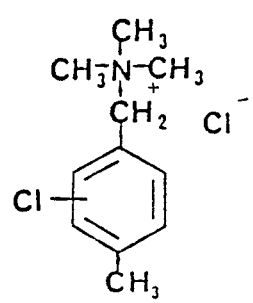
(II)
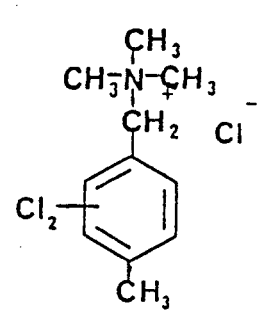
(III)
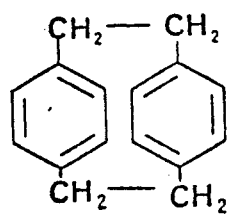
(A)
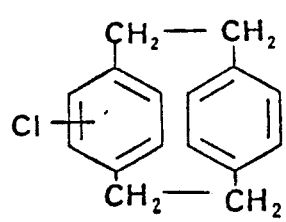
(B)
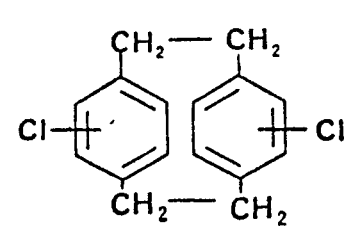
(C)
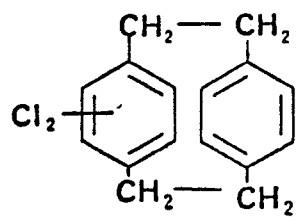
(D)
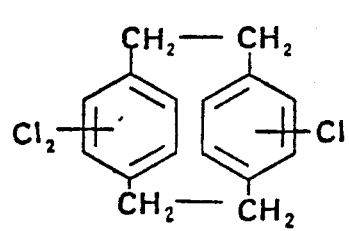
(E)
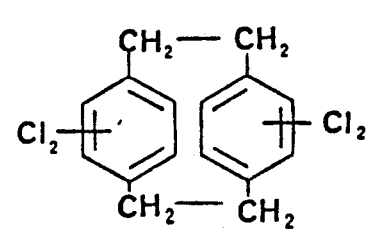
(F)

PROCESS FOR THE PREPARATION OF MIXED PARYLENE DIMERS FREE OF ALPHA-HALOGENS

BACKGROUND OF THE INVENTION

1) Field of the Invention

This invention relates in general to a process for the preparation of mixed parylene dimers. In one aspect, this invention is directed to a process for the preparation of a mixture of parylene dimers which are free of alpha-halogens and wherein the dimer distribution in the mixture imparts desirable properties to parylene films and coatings prepared therefrom. In a further aspect, this invention relates to a process for preparing a mixture containing parylene dimers which are free of alpha-halogens and thereby avoid the environmentally undesirable formation of acid halides during deposits of parylene films and coatings. In another aspect, the invention is directed to compositions comprised of a blend of various dimers.

2) Background of the Related Art

Parylene is a generic term applied to a class of poly-p-xylylenes which are derived from a dimer of the structure:

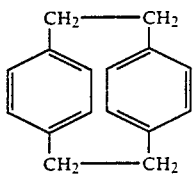

Parylene is an inert, transparent, conformal coating which has excellent barrier properties and can be used at relatively high temperatures. Due to its ability to provide thin films and conform to substrates of varied geometric shapes, it is ideally suited for use as a conformal coating in a wide variety of fields, particularly in the electronics industry.

The term "parylene" as employed throughout the specification and appended claims is intended to encompass not only those products prepared by the vapor deposition of the p-xylylenes of formula (I) above, but other known parylenes prepared from p-xylylenes containing one or more substituents on the aliphatic or aromatic portion of the molecule.

The preparation of p-xylylene polymers by various routes has been reported in the patent literature. For example, U.S. Pat. No. 2,719,131 which issued in Sep. 27, 1955 to E. I. DuPont de Nemours and Company disclosed a process for preparing poly-p-xylene wherein the vapors of p-xylylene were pyrolyzed in the presence of chlorine gas.

Also in British patent number 650,947 which was granted Mar. 7, 1951, polymer formation was detected on the walls of a cooling chamber after p-xylylene was vaporized and pyrolyzed.

In U.S. Pat. No. 3,149,175 which issued Sep. 15, 1964 a process was reported for the preparation of di-para-xylylenes in yields of 10 percent and higher. The process involved pyrolyzing a mixture of steam and p-xylene at a temperature between about 800° C. and 1000° C. to generate a free radical and condensing the reactive diradical in a fluid medium.

The preparation of para-xylylene polymers was also disclosed in U.S. Pat. No. 3,342,754 which issued on Sep. 19, 1967 to W. F. Gorham and is assigned to Union Carbide Corporation. In this patent it is indicated that true linear homopolymers of para-xylylene could be produced in nearly quantitative yields by heating a cyclo-di-para-xylylene having up to 6 aromatic nuclear substituent groups to a temperature between about 450° C. and 700° C. for a time sufficient to cleave substantially all of the di-para-xylylene into vaporous para-xylylene diradicals and cooling the vaporous diradicals to a temperature below the condensation temperature.

Although a wide variety of methods have been reported in the literature for the preparation of parylene dimers, there have been no reports in the prior art relative to the use of mixtures or blends of different dimers which are entirely free of alpha-halogens and wherein the physical and/or chemical properties of parylene films and coatings can be varied.

Prior to the present invention when parylene coatings, films and the like were prepared, one would merely prepare the individual dimers, purify them and select the individual dimer which gave the properties closest to that desired and then utilize the starting compounds and deposition conditions most suitable for that particular dimer. No effort had been made to prepare a dimer mixture or blend having a predetermined distribution of non-halogenated, partially halogenated and fully halogenated paracyclophanes in order to control or vary the properties of the resulting coating or film.

It has been observed, however, that the properties, composition and deposition conditions of parylene films and coatings prepared from dimers, will vary depending upon the particular 2,2-paracyclophane dimer employed. Thus, in the past, 2,2-paracyclophane, monochloro-2,2-paracyclophane, dichloro-2,2-paracyclophane and tetrachloro-2,2-paracyclophane when subjected to vapor deposition conditions, each gave films and coatings having a variety of chemical and physical properties. Although it had been possible to prepare mixtures or blends of dimers of the substituted and unsubstituted 2,2-paracyclophanes, prior to the present invention such mixtures had not been prepared by the Hofmann elimination of a mixture of quaternary ammonium salts.

It has been noted that the preparation of dimers containing ring halogens by the chlorination of paracyclophane usually results in halogenation of at least some of the aliphatic carbon atoms. When these halogenated dimers are subjected to vapor deposition conditions for the formation of parylene films and coatings, the less firmly bonded aliphatic halogens are released and can form acid halides which require environmentally safe methods of disposal.

It is therefore an object of the present invention to provide a process for the preparation of mixed parylene dimers which are useful for the preparation of parylene films and coatings. Another object is to provide a process for preparing a mixture of halogenated and non-halogenated dimers of 2,2-paracylophanes wherein the distribution of monohalo- polyhalo- and unsubstituted dimers can be varied so as to alter the properties of the resulting films and coatings. A further object of the present invention is to provide a method for the preparation of blends of halogenated and non-halogenated paracyclophanes which are free of alpha-halogen substitution on the aliphatic carbon atoms.

In another object, the invention provides blends and mixtures of halogenated paracyclophanes containing halogen atoms only on the ring carbon atoms. A still further object is to provide an environmentally safe method for the vapor deposition of parylene from blends of halogenated paracyclophanes, which method avoids the formation of acid halides. A further object of the present invention is to provide a process for preparing the mixture of dimers which avoids the preparation and purification of the individual dimers. A further object is to provide articles coated with parylene which have been prepared by the vapor deposition of the dimer mixture. Another object of the invention is to provide a process for preparing a mixture of halogenated and nonhalogenated dimers of 2,2-paracyclophanes wherein the distribution of monohalo, polyhalo and unsubstituted dimers can be varied so as to alter the properties of the resulting parylene films and coatings. Another object of the invention is to provide a process which is simple and efficient and hence is effective in reducing the overall cost in the preparation of the paracyclophane dimer mixtures or blends. A further object of this invention is to provide a process for the preparation of the dimer mixture which provides even higher yields by utilizing dimethylsulfoxide in combination with a selected class of reaction promoters. These and other objects will readily become apparent to those skilled in the art in the light of the teachings herein set forth.

SUMMARY OF THE INVENTION

In its broad aspect, the present invention relates to the preparation of a mixture of halogenated and non-halogenated 2,2-paracyclophanes, coatings and films prepared by the vapor deposition of parylene from such mixtures and articles coated with parylene. The process for the preparation of the mixture of halogenated and non-halogenated 2,2-paracyclophanes used in the preparation of parylene, comprises the steps of:
 a) forming a starting mixture of at least two of:
  i) p-methylbenzyltrimethylammonium halide,
  ii) p-methyl-monohalobenzyltrimethylammonium halide, and
  iii) p-methyl-dihalobenzyltrimethylammonium halide,
 b) contacting the mixture with an alkaline hydroxide, and
 c) thereafter recovering the mixture.
Articles can be coated and films prepared by the vapor deposition of parylene onto various substrates. One of the main utilities of parylene has been, and continues to be, is its use as a conformal coating for a variety of articles, such as electronic circuit boards, and the like. Additionally, parylene has found wide acceptance in a wide variety of other fields due to its desirable properties.

DESCRIPTION OF THE DRAWING

A more detailed understanding of the invention will be had by reference to the drawing wherein the single FIGURE is a flow diagram showing a mixture containing the three p-methylbenzylmethyulammonium halide compounds and the various dimers resulting from the Hofmann elimination reaction of the mixture or blend.

DESCRIPTION OF THE PREFERRED EMBODIMENTS

As indicated previously, although a wide variety of method have been reported in the literature for the preparation of parylene dimers, there is nothing in the literature relative to the use of mixtures of dimers which have been prepared by the Hofmann elimination reaction of a mixture of p-methylbenzylmethylammonium halides.

In European patent publication 0 252 402 and 0 253 191 there are disclosed processes for the preparation of 2,2-paracyclophanes and certain derivatives, including halo-substituted derivatives, p-methylbenzyltrimethylammonium hydroxide by the Hofmann elimination reaction. However, the preparation of a mixture of dimers form a mixture of hydroxides is not disclosed. European patent publication 0 183 083 discloses the preparation of 2,2-paracyclophane from the halide salt but does not disclose any dimers with ring substitutents.

As indicated above, and as is shown in the drawing, a mixture of the 2,2-paracyclophane dimers is conveniently prepared by the Hofmann elimination reaction of the quaternary ammonium salts. The drawing clearly shows that from a initial mixture of p-methylbenxyltrimethylammonium chloride, (I), 2(3)-chloro-p-methylbenxyltrimethylammonium chloride, (II), and dichloro-p-methylbenzyltrimethylammonium chloride, (III), a mixture can be obtained containing six structurally different dimers (A)-(f), each of which can influence the final products in the vapor deposited parylene coating.

In addition to the above advantages for preparing the blends of the halogenated and non-halogenated dimers, the process of the present invention provides a unique method for utilizing the dimers in an environmentally safe way in the deposition of parylene films and coatings.

By preparing the dimers from halogenated and non-halogenated Q-salts, one avoids the presence of and halogen atoms on the aliphatic carbon atoms which join the two cyclohexyl rings. Since the Q-salts can only contain ring halogens, it is impossible when they undergo dimerization to have any halogens present on the aliphatic carbon atoms.

It is known that cycloparaphanes which undergo halogenation, (i.e., halogenation after dimerization of the Q-salts) will always have some halogens present on the aliphatic carbon atoms. These halogens atoms are not firmly bonded to the aliphatic carbon atoms as are the ring halogen atoms. Accordingly, when the dimers are heated under vapor deposition conditions to form parylene, some of these weaker bonded halogens are released and form acid halides, such as hydrochloric acid within the deposition chamber. Hydrochloric acid is not an environmentally desirable by-product and care must be taken in order to comply with proper disposal requirements. Also, in addition to environmental concerns, hydrochloric acid can also be detrimental to the equipment and adversely effect the polymerization of the dimers themselves.

Prior to the present invention when parylene coatings, films and the like were prepared, one would merely select the dimer which gave the properties closest to that desired in the final product and utilize the starting compounds and deposition conditions most suitable for that particular dimer. No efforts have been made to prepare a dimer mixture having a distribution of non-halogenated, partially halogenated or fully halogenated ring atoms of the dimer in order to control properties of the resulting coating or film.

It has been observed, however, that the properties, composition and deposition conditions of parylene films and coatings will vary depending upon the particular 2,2-paracyclophane dimer employed. Thus, in the past, 2,2-paracyclophane, 2,2-monohalo-2,2-parayclophane, dichloro-2,2-paracyclophane, trichlor-2,2-paracyclophane, and tetrachloro-2,2-paracyclophane when subjected to vapor deposition conditions, each gave films and coating having chemical and physical properties peculiar to the particular starting dimer. Although it has been possible to prepare mixtures of dimers from two or more substituted or unsubstituted 2,2-paracyclophanes, prior to the present invention such mixtures had not been prepared by the Hofmann elimination of a mixture of quaternary ammonium salts.

Moreover, as indicated above, halogenated cycloparaphanes have customarily been prepared by halogenation after formation of the dimer whch usually results in some halogenation of the aliphatic carbon atoms. Under vapor deposition conditions, acid halides formed by the release of these halogens which can present environmental problems with respect to their disposal.

In practice, the formation of the dimers of the present invention is conducted under conditions suitable for the Hofmann elimination reaction to proceed and wherein the formation of the dimer is favored over the formation of the polymerized product, i.e.,parylene. It has been found that best results are obtained when the reaction is conducted in a two phase system comprised of water and an organic phase. The starting material, i.e., the p-methylbenzyltrimethylammonium hydroxide compounds are preferentially soluble in the aqueous phase whereas the dimer is preferentially soluble in the organic phase. Any undesirable polymer formation usually occurs at the boundary between the two phases. Thus, there is always the undesirable competing reaction for polymer formation.

The reaction as indicated is conducted in an aqueous phase and an organic phase. The organic phase is one in which the dimer is soluble and which the starting p-methylbenzyltrimethylammonium hydroxides are largely insoluble. A wide variety of organic materials can be employed as the organic medium and include such compounds as benzene, toluene, the xylenes, such as para-xylene, ortho-xylene, meta-xylene, hexane, octane, methylene chloride and the like.

In practice, it is possible to prepare mixtures of dimers which range from those having a relatively high concentration of the non-halogenated dimer to those having a high concentration of the tetra-halogenated dimer. For example, concentrations can range from 0 to about 99 weight percent of each of the Q-salts (I)-(III) shown in the drawing, with the total, of course, not exceeding 100 percent, and at least two different Q-salts being present. A typical dimer mixture can contain aproximately equal amounts of the three dimers. It is also possible to prepare a mixture of dimers of the Q-salts which will provide essentially the same dimer as the halogenated isomer mixtures commercially available and obtained by the partial halogenation of the dimer after formation.

It has been noted that in order to achieve optimum yields of the desired dimer on a consistent basis, the mole ratio of the components in the reaction mixture should be within certain specific ranges as indicated below:

a) the mole ratio of alkaline hydroxide to the quaternary ammonium salts should be within the range of from about 2:1 to about 20:1, and preferably from about 2:1 to about 12:1.

b) the mole ratio of water to the quaternary ammonium salts should be within the range of from about 20:1 to about 70:1 and preferably from about 0:1 to about 50:1.

c) the mole ratio of organic solvent to the quaternary salt is not necessarily critical, but good results are obtained when the mole ratio of solvent to the quaternary salts is within the range of from about 10:1 to about 80:1 and more preferably from about 20:1 to about 60:1.

It has also been observed that the yield of the desired dimer mixture or blend can be increased by the use of dimethylsulfoxide in the Hofmann elimination reaction. Moreover, the yield of the dimer mixture or blend could be increased even further if certain reaction promoters were also employed in the reaction system. In the past, only small increases in yields were obtainable in the preparation of the individual dimers and hence the cost of the process remained exceedingly high and therefore the application of parylene conformal coatings was limited to the preparation of relatively expensive materials. For the most part the use of parylene had been confined to the military or those applications in the electronics industry where the cost of the final product could justify the use of the expensive coating process.

The reaction promoters employed in the process of the present invention are those promoters which, when employed with dimethylsulfoxide, promote the Hofmann elimination reaction so as to shift the equilibrium of the reaction to favor the formation of the dimer mixture or blend as opposed to the competing reaction which favors polymer formation. The exact mechanism by which the reaction promoters operates is not readily apparant but it is believed that the presence of the promoters plays a critical part in promoting the reaction to dimer formation while retarding the reaction of the dimer so formed from polymerizing to parylene.

It has been found that a limited number of specific reaction promoters are suitable for use in the process of the present invention, and that such promoters must be used in a specific combination if increased yields of the dimer are to be obtained.

The reaction promoters which have been found to be suitable for optimizing the yield of dimer by the process of the present invention can be classified into different categories.

A first class of compounds which can be employed as reaction promoters in the process of the present invention are the crown ethers. These are the cyclic ethers composed of carbon, oxygen and hydrogen. In practice, crown ethers containing from 4 to 6 oxygen atoms and from 12 to 18 carbon atoms can be employed in the process of the present invention. Particularly preferred is 18 crown 6.

Illustrative crown ethers which are suitable for use in the process of this invention are ethers such as 12 Crown 4 (1,4,7,10-tetraoxacyclododecane), 15 Crown 5 (1,4,7,10,13-pentaoxacyclopentadecane), 18 Crown 6 (1,4,7,10,13,16-hexaoxacyclooctadecane), benzo-15 Crown 5, bis(benzo 15 Crown 5)methyl]pimelate, bis[(12 Crown 4) 2-ylmethyl]2-dodecyl-2methyl malonate, dibenzo 18 Crown 6, dibenzo 24 Crown 6, dicyclohexano 18 Crown 6, dicyclohexano 18 Crown 6, and dicyclohexano 24 Crown 8 and the like.

A second class of reaction promoters suitable for use in the present process, are the alkoxy alkyl and the polyalkyleneoxy alkyl ethers. These compounds are sometimes referred to as "glymes" particularly when the ether is capped with a methoxy group, and include the diglymes and the tetraglymes.

Illustrative compounds within this class include amoung others, the methyl methoxyethyl ethers of the formula:

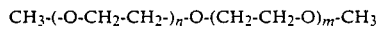

CH$_3$-(-O-CH$_2$-CH$_2$-)$_n$-O-(CH$_2$-CH$_2$-O)$_m$-CH$_3$ wherein n has a value of from 1 to 18, and more preferably from 2 to 4, and m is 0 or 1 to 4.

A further class of reaction promoters which can be employed in the process of the present invention are the alkyl substituted imidazolidinones. Such compounds include those having from 2 to 4 lower alkyl groups attached to the ring carbon or nitrogen atoms. Preferably the lower alkyl groups contain from 1 to 6 carbon atoms and more preferably 1 to 2 carbon atoms. The methyl-substituted imidazolidinones are the most preferred.

Illustrative compounds include 1,3-dimethyl-2-imidiazolidinone, 1,3,4-trimethyl-2-imidazolidinone, 1,3,4,5-tetramethyl-2-imidazolidinone, 1,3-diethyl-2-imidazolidinone, 1,2-dimethyl-3-ethyl-2-imidazolidinone, and the like.

It has been observed that the best results are obtained in formation of the dimer mixtures or blends when the dimethylsulfoxide and the reaction promoters are employed in certain amounts as follows:

a) the mole ratio of dimethylsulfoxide to the quaternary ammonium salts should be within the range of from about 2:1 to about 30:1, and preferably from about 8:1 to about 20:1.

b) the mole ratio of the total reaction promoters to the quaternary salts should be within the range of from about 20:1 to about 1:1.

In practice it has been observed that when the reaction promoter is a glyme it should be present within the range of from about 4:1 to about 8:1. The mole ratio of the 18 crown 6 to the quaternary salts should be within the range of from about 3:1 to about 1:1.

As indicated previously, by employing reaction promoters in conjunction with the dimethylsulfoxide, markedly increased yields of the dimer can be obtained while polymer formation is minimized.

In order to obtain optimum yields of the desired dimer, the choice of reaction promoters employed is important. It has been observed that at least one of the promoters used in combination with DMSO must be a glyme to provide the highest yields in the shortest reaction period.

In practice, it has been observed that the concentration of the dimethylsulfoxide is important and not the feed configuration. Thus, in contrast to the prior art, all of the components in the present invention can be added together at one time and none need to be added dropwise. This can be a great saving in time over the processes disclosed in the prior art. It is also evident from operations that the mole ratio of the DMSO to quaternary salt is important if optimum yields are to be obtained. Additionally, it has been noted that DMSO in the presence of water and caustic can decompose at high temperatures and hence it is preferred to employ lesser amounts of DMSO when the reaction promoters of the present invention are used.

In actual practice of the process of the present invention, the mixture is stirred to insure intimate mixing of the organic and aqueous phases. Thereafter the phases are separated and the dimer mixture or blend recovered from the organic phase and purified according to known techniques.

As indicated above, the process of the present invention is preferably conducted at a temperature between about 20° and about 130° C., and more preferably between about 25° and about 120° C. Temperatures above and below this range can be employed but are less preferred.

Pressure is not critical and the reaction can be conducted at atmospheric, subatmospheric or super atmospheric pressures.

The p-methylbenzyltrimethylammonium hydroxides are well known compound and have been reported in the literature. If desired, they can be prepared in situ by reaction of a base on the corresponding quaternary ammonium salt such as the halide.

As indicated above, parylene is an excellent, inert, transparent conformal coating which, due to its unusual properties, renders it particularly suitable for a wide variety of applications particularly in the electronics industry. Methods of applying the coatings starting from the dimer, and equipment for effecting such applications are all well known and readily available.

The following examples illustrate the best mode presently contemplated for the practice of this invention.

EXAMPLE 1

Preparation of Mixed Paracyclophane Dimers

A mixture of 4400 grams of p-xylene, 976 grams of DMSO, 52 grams of water, 100 grams of p-methylbenxyltrimethylammonium chloride, 500 grams of 2-chloro-p-methylbenxyltrimethylammonium chloride, and 101 grams of dichloro-p-methylbenzyltrimethylammonium chloride, were charged to a 12 liter glass reactor equipped with stirrer, condenser and nitrogen purge. The mixture was stirred at room temperature while 904 grams of 50 percent aqueous sodium hydroxide was slowly fed into the reactor over a period of approximately 2 hours. Upon completion of the addition of the hydroxide, the temperature in the reactor was 27° C. Thereafter, the reactor was heated at about 45° C. over a two hour period. The next day the mixture was heated to about 90° C. over a period of 20 hours. The mixture was cooled, filtered, washed with water and the mixed dimer was recovered.

EXAMPLE 2

Preparation of Mixed Paracyclophane Dimers

A mixture of 4400 grams of p-xylene, 975 grams of DMSO, 52 grams of water, 200 grams of p-methylbenxyltrimethylammonium chloride, 300 grams of 2-chloro-p-methylbenxyltrimethylammonium chloride, and 200 grams of dichloro-p-methylbenzyltrimethylammonium chloride, were charged to a 12 liter glass reactor equipped with stirred and condenser. The mixture was stirred at room temperature while 906 grams of 50 percent aqueous sodium hydroxide was slowly fed into the reactor over a period of approximately 2.0 hours. Upon completion of the addition of the hydroxide, the temperature in the reactor was 27° C. Thereafter, the reactor was heated at about 42° C. over a two hour period. The next day the mixture was heated to about 75° C. over a period of 8.0 hours. The mixture was cooled, filtered, washed with 34.2 grams of water and the mixed dimer was recovered.

EXAMPLE 3

Preparation of Mixed Paracyclophane Dimers

A mixture of 4400 grams of p-xylene, 968 grams of DMSO, 51 grams of water, 100 grams of p-methylbenxyltrimethylammonium chloride, 300 grams of 2-chloro-p-methylbenxyltrimethylammonium chloride, and 300 grams of dichloro-p-methylbenzyltrimethylammonium chloride, were charged to a 12 liter glass reactor equipped with stirred and condenser. The mixture was stirred at room temperature while 904 grams of 50 percent aqueous sodium hydroxide was slowly fed into the reactor over a period of approximately 2.5 hours. Upon completion of the addition of the hydroxide, the temperature in the reactor was 27° C. Thereafter, the reactor was heated at about 45° C. over a two hour period. The next day the mixture was heated to about 75° C. over a period of 8.0 hours. The mixture was cooled, filtered, washed with 34.5 grams of water and the mixed dimer was recovered.

EXAMPLE 4

Parylene films were prepared from the dimer mixtures of Examples 1-3 by a vapor deposition process in accordance with known techniques. The films were deposited on aluminum coupons approximately 1" by 3" in size and evaluated for film thickness, clarity, mass, and electrical properties (voltage breakdown). Variations were noted among the different blends of dimers.

EXAMPLES 5-10

Preparation of Mixed Paracyclophane Dimers

In a manner similar to that employed in Examples 1-3, other dimer mixtures are prepared wherein the starting p-methylbenzyltrimethylammonium halides are employed in the amounts indicated in Table I below:

TABLE I

| Example | Amount of Starting Halide (% by Wt) | | |
|---|---|---|---|
| | I | II | III |
| 5 | 30 | 40 | 30 |
| 6 | 30 | 30 | 40 |
| 7 | 20 | 40 | 40 |
| 8 | 10 | 50 | 40 |
| 9 | 50 | 50 | 0 |
| 10 | 50 | 0 | 50 |

I = p-methylbenzyltrimethylammonium chloride
II = p-methyl-monochlorobenzyltrimethylammonium chloride.
III = p-methyl-dichlorobenzyltrimethylammonium chloride.

Although the invention has been illustrated by the preceding examples, it is not to be construed as being limited to the materials employed therein, but rather the invention is directed to the generic area as hereinbefore disclosed. Various modifications and embodiments thereof may be made without departing from the spirit or scope thereof.

What is claimed is:

1. An environmentally improved process for the preparation of a mixture of halogenated and non-halogenated 2,2-paracyclophanes used in the preparation of parylene, and wherein said mixture has a predetermined distribution of halogenated isomers which are free of alpha-isomers, which process comprises the steps of:
   a) forming a starting mixture of at least two of:
      i) p-methylbenzyltrimethylammonium halide,
      ii) p-methyl-monohalobenzyltrimethylammonium halide, and
      iii) p-methyl-dihalobenzyltrimethylammonium halide, wherein the ratio of (i), (ii) and (iii) in the starting mixture is selected to provide a predetermined distribution of halogenated isomers;
   b) contacting said mixture with an alkaline hydroxide, and
   c) thereafter recovering said mixture.
2. The process of claim 1 wherein the process is effected in the presence of an inert water-immiscible organic solvent.
3. The process of claim 2 wherein said solvent is selected from the group of benzene, toluene, para-xylene, ortho-xylene, meta-xylene, hexane, octane, and methylene chloride.
4. The process of claim 1 wherein said alkaline hydroxide is sodium hydroxide.
5. The process of claim 1 wherein said alkaline hydroxide is potassium hydroxide.
6. The process of claim 1 wherein said halide is chloride.
7. The process of claim 1 wherein said halo is chloro.
8. The process of claim 1 wherein said starting mixture is comprised of:
   1) from about 0 to about 99% by weight of p-methylbenzyltrimethylammonium halide,
   2) from about 0 to about 99% by weight of p-methyl-monohalobenzyltrimethylammonium halide, and
   3) from about 0 to about 99% by weight of p-methyl-dihalobenzyltrimethylammonium halide.
9. The process of claim 8 wherein said halide is chloride.
10. The process of claim 8 wherein said halo is chloro.
11. The process of claim 1 which is conducted in the presence of dimethylsulfoxide and at least one reaction promoter.
12. The process of claim 11 wherein said reaction promoter is selected from the group consisting of:
   a) a methyl methoxyethyl ether of the formula:

$CH_3\text{-(-O-CH}_2\text{-CH}_2\text{-)}_n\text{-O-(CH}_2\text{-CH}_2\text{-O)}_m\text{-CH}_3$ wherein n has a value of from 1 to 18, and m is 0 or 1 to 4,
   b) a crown ether having from 4 to 6 oxygen atoms and from 12 to 18 carbon atoms, and
   c) an alkyl-substituted imidazolidinone.
13. The process of claim 12 wherein said crown ether is 1,4,7,10,13,16-hexaoxacyclooctadecane.
14. The process of claim 12 wherein said methoxyalkenyloxyether is diglyme.
15. The process of claim 14 wherein said diglyme is 2-methoxyethylether.
16. The process of claim 12 wherein said methoxyalkoxyether is a tetraglyme.
17. The process of claim 16 wherein said tetraglyme is 2-butoxyethyl ether.
18. The process of claim 12 wherein said alkyl-substituted imidazolidinone is 1,3-dimethyl-2-imidazolidinone.
19. A mixture of halogenated and non-halogenated 2,2-paracyclophanes prepared in accordance with claim 1.
20. A parylene coating or film prepared by vapor deposition of the mixture of claim 19.
21. An article having a parylene coating of claim 20.

* * * * *